(12) United States Patent
Ishii et al.

(10) Patent No.: US 8,394,417 B2
(45) Date of Patent: Mar. 12, 2013

(54) METHOD OF PRODUCING A DRY EARTHWORM POWDER

(75) Inventors: Yoichi Ishii, Miyazaki (JP); Kazuyuki Ishii, Miyazaki (JP); Hiroyuki Sumi, Kurashiki (JP); Etsuo Yoshida, Miyazaki (JP); Sayaka Ishii, Miyazaki (JP)

(73) Assignee: Well Stone Co., Miyazaki (JP)

( * ) Notice: Subject to any disclaimer, the term of this patent is extended or adjusted under 35 U.S.C. 154(b) by 237 days.

(21) Appl. No.: 12/903,615

(22) Filed: Oct. 13, 2010

(65) Prior Publication Data

US 2011/0086106 A1    Apr. 14, 2011

(30) Foreign Application Priority Data

Oct. 13, 2009    (JP) ................ 2009-236514

(51) Int. Cl.
*A61K 35/56*    (2006.01)
(52) U.S. Cl. ......................................................... 424/520
(58) Field of Classification Search .................... 424/520
See application file for complete search history.

(56) References Cited

U.S. PATENT DOCUMENTS

| | | | |
|---|---|---|---|
| 5,024,844 A | 6/1991 | Ishii et al. | |
| 5,186,944 A | 2/1993 | Ishii et al. | |
| 8,137,701 B2 * | 3/2012 | Ishii et al. | 424/520 |
| 2008/0206352 A1 | 8/2008 | Li | |
| 2009/0238891 A1 | 9/2009 | Ishii et al. | |

FOREIGN PATENT DOCUMENTS

| | | |
|---|---|---|
| JP | 64-47718 | 2/1989 |
| JP | 64-47719 | 2/1989 |
| JP | 64-47720 | 2/1989 |
| JP | 1-268639 | 10/1989 |
| JP | 3-72427 | 3/1991 |
| JP | 2008-81476 | 4/2008 |
| KR | 10-2008-0033430 | 4/2008 |

OTHER PUBLICATIONS

Korean Office Action (with partial English translation) issued May 17, 2012 in corresponding Korean Patent Application No. 10-2010-0088825.

* cited by examiner

*Primary Examiner* — Ruth Davis
(74) *Attorney, Agent, or Firm* — Wenderoth, Lind & Ponack, L.L.P.

(57) ABSTRACT

Provided is a simple and easy method of producing an innoxious dry earthworm powder, while suppressing inactivation of the enzymes contained in earthworms. In the method, a homogenate obtained by grinding living earthworms is freeze-dried and the dried product is heat-treated at a temperature of 110° C. or higher but lower than 130° C. Preferably, the method according to the present invention comprises further a process for preparation of the living earthworms, which precedes the grinding step, comprising the steps of: standing the living earthworms under light for 10 to 50 hours; removing the dirt formed on the skin thereof, bringing the earthworms into contact with an organic acid for 30 seconds or less; diluting the acid with addition of water to adjust the pH of the aqueous acidic solution to a pH in the range of 2 to 5; standing the earthworm mixture under the pH condition for 3 to 180 minutes; and then washing the earthworms with water.

12 Claims, 1 Drawing Sheet

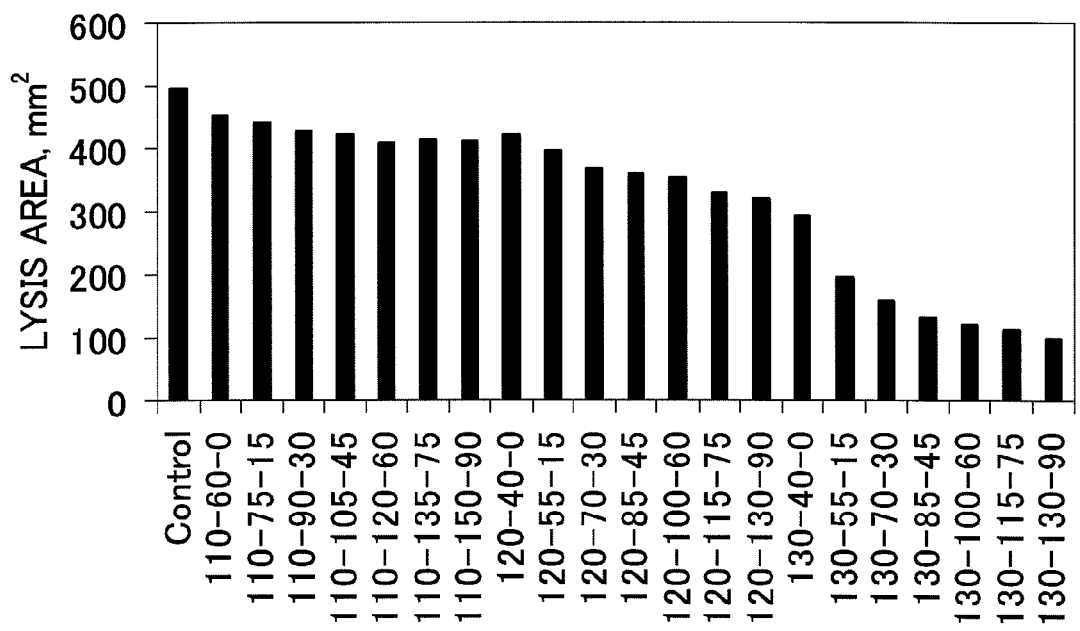

METHOD OF PRODUCING A DRY EARTHWORM POWDER

FIELD AND BACKGROUND OF THE INVENTION

The present invention relates to a method of producing a dry earthworm powder, in particular to a method of producing an innoxious dry earthworm powder while suppressing inactivation of the enzymes contained in an earthworm.

Earthworms have been used from ancient times in oriental countries as drugs for prevention and treatment of various diseases, and have found applications such as intracystic calculus-contraction and releasing-stimulating agent, anti-choloplania agent, parturifacient, tonic, hair growth tonic, pickup, antifebrile, spasm-treating agent, blood flow accelerator, hemiplegia-treating agent, indirect analgesic, urination improving agent, anti-bronchial asthma agent, anti-hypertension agent and others.

It is necessary to remove the dirt of earthworm remaining in the digestive tracts, the deposit on the skin, and others for production of a medicine for oral administration by using the earthworm as the raw material, and various methods for that purpose have been proposed.

Examples thereof so far proposed include methods of producing a dry earthworm powder useful as an anti-diabetes agent, anti-hyperlipidemia agent, or blood pressure-adjusting agent, by immersing living bodies of earthworms in an aqueous solution of an alkali salt such as sodium salt or potassium salt, allowing them to excrete the cast in the digestive tracts, wet-grinding the earthworms, and freeze-drying the suspension thus obtained under vacuum (JP64-47718A, JP64-47719A, JP64-47720A and JP01-268639A), and a method of producing a medicine for patients with thrombosis, by immersing living bodies of earthworms in an aqueous acid solution kept at 6 to 26° C. for 0.1 to 5 hours, allowing them to excrete the cast in the digestive tracts, grinding the earthworms, degassing the homogenate, and vacuum-drying the homogenate, while the temperature is raised stepwise (JP03-72427A).

The inventors have also proposed a method of making earthworm excrete its content in the digestive tract by placing the earthworm under an environment in unpleasant habitat condition generated with organic acid (JP2008-081476A).

However, earthworm powders produced by conventional production methods had a problem that microbes contained in the earthworm are not sufficiently sterilized, depending on the drying step by vacuum freeze-drying and the like. Although measures such as alcohol sterilization were taken, these measures also had problems of increased labor and elongated period and thus of increased cost, and thus, there existed a demand for measures to solve the problems.

SUMMARY OF THE INVENTION

An object of the present invention is to provide a simple and easy method of producing an innoxious dry earthworm powder, while suppressing inactivation of the enzymes contained in the earthworm.

After intensive studies to solve the problem above, the inventors have found that it is possible to solve it by heating the earthworm powder at a particular temperature after freeze-drying, and made the present invention.

Generally, enzymes are commonly known to be fragile to heat, except those in some thermophilic bacteria, and thus, heat treatment at up to about 80° C. has been conducted but heat treatment at a temperature higher than that has not been discussed yet. However, the inventors have focused on the fact that heat treatment is the safest, simplest and most convenient method among the studied methods of sterilizing an earthworm powder and studied the optimal heating temperature. As a result, they have found that the activity of the enzymes contained in an earthworm powder was preserved even if the earthworm powder was heated to a temperature drastically higher than that used in other methods.

Specifically, the method of producing a dry earthworm powder according to the present invention comprises the steps of grinding living earthworms into a homogenate; freeze-drying the homogenate; and heat-treating the dried product at a temperature in the range of 110° C. or higher but lower than 130° C.

Preferably, the method of producing a dry earthworm powder according to the present invention comprises further a process for preparation of the living earthworms, which precedes the grinding step, comprising the steps of:

standing the living earthworms under light for 10 to 50 hours;
removing the dirt formed on the skin thereof,
bringing the earthworms into contact with an organic acid for 30 seconds or less;
diluting the acid with addition of water to adjust the pH of the aqueous acidic solution to a pH in the range of 2 to 5;
standing the earthworm mixture under the pH condition for 3 to 180 minutes; and then washing the earthworms with water.

Alternatively, the method of producing a dry earthworm powder according to the present invention comprises further a process for preparation of the living earthworms, which precedes the grinding step, comprising the steps of:

standing the living earthworms under light for 10 to 50 hours;
removing the dirt formed on the skin thereof,
immersing the earthworms in a solution of an organic acid having a pH adjusted beforehand in the range of 2 to 5;
standing the earthworm mixture under the pH condition for 3 to 180 minutes; and then washing the earthworms with water.

Also, the method of producing a dry earthworm powder according to the present invention comprises further a process for preparation of the living earthworms, which precedes the grinding step, comprising the steps of:

standing the living earthworms under light for 10 to 50 hours;
removing the dirt formed on the skin thereof,
bringing the earthworms into contact with a crystalline hydroxycarboxylic acid powder for 30 seconds or less;
diluting the acid with addition of water to adjust the pH of the aqueous acidic solution to a pH in the range of 2 to 5;
standing the earthworm mixture under the pH condition for 3 to 180 minutes; and then washing the earthworms with water.

Further, in the method of producing a dry earthworm powder according to the present invention, it is preferable that the water washing is carried out with water containing micro-nano bubbles.

Furthermore, in the method of producing a dry earthworm powder according to the present invention, it is preferable that the freeze-drying is carried out under vacuum after the homogenate is frozen at −18° C. to −35° C. for 20 to 240 hours.

The present invention can provide a simple and easy method of producing an innoxious dry earthworm powder while suppressing inactivation of the enzymes contained in the earthworm.

BRIEF DESCRIPTION OF THE DRAWING

FIG. 1 is a graph showing the results in Examples 1 and 2 and Comparative Example 1.

DETAILED DESCRIPTION OF EXEMPLARY EMBODIMENTS

Hereinafter, the method of producing a dry earthworm powder according to the present invention will be described in detail.

In the method according to the present invention, living earthworms are used as the raw material, and examples of the living earthworms include *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* Iizuka, *Tubifex hattai* Nomura, *Limnodrilus gotoi* Hatai (*L. socialis* Stephenson) and so on.

Preparation of the Living Earthworms for Use in the Inventive Method before grinding is not particularly limited, but can be carried out, for example, in the following way. First, living earthworms collected from culture bed are transferred into a flat box such as bread box and kept therein for 10 to 50 hours, preferably for one day. The content of the living earthworms in the box should be an amount corresponding to a thickness of 30 to 60 mm, preferably 40 to 50 mm. Care should be given to ensure that no foreign materials such as sand and mud remain in the flat box, and the flat box should be kept bright at night, as in light culture, because the earthworms are nocturnal and active in living activity in dark place and thus may consume their physical strength. The living earthworms show their self-protecting function under the treatment, to preserve their living environment by excreting the digests remaining in the digestive tracts, covering the entire bodies with the excrete, and thus preventing vaporization of water, and it is possible finally to remove the digests in the digestive tracts and the stains deposited on their skins almost completely, by removing the stains, i.e., the excrete, covering the earthworms repeatedly by using a suitable means. The removal of the stains deposited on the skins can be carried out by covering the living earthworms, for example, with a nonwoven fabric and thus allowing adsorption of the stains.

Then, the living earthworms, from which the stains are thus removed, are preferably exposed directly to a living environment unpleasant to the living earthworms. Such a treatment makes the living earthworms try to improve the living environment by excreting the body fluid by their self-protecting function and thus, it is possible to make the earthworms excrete not only the digests remaining in the digestive tracts, but also ammonia, a cause of foul odor, as well as the body fluid containing arsenic that is toxic to the body.

An example of the method of generating an unpleasant living environment is to bring the living earthworms into contact with an organic acid. A living environment unpleasant to the living earthworms can be formed immediately by bringing the earthworms into contact with the organic acid. As for the contact with the organic acid, an organic acid powder may be sprayed directly or as a concentrated aqueous organic acid solution on the living earthworms. Examples of the organic acids used then include acetic acid, malic acid, citric acid, lactic acid, malonic acid, succinic acid and the like. These acids may be used alone or as a mixture of two or more acids. The particularly favorable organic acid is citric acid. If such an unpleasant living environment is generated as described above, prolonged contact between the living earthworms and an organic acid powder or a conc. aqueous organic acid solution leads to death of the earthworms with loss of living functions and thus to no excretion of the digest in the digestive tracts, and therefore, the organic acid should be diluted with water as soon as possible, normally within 30 seconds or less, preferably 20 seconds or less to adjust the pH of the aqueous acidic solution to a pH in the range of 2 to 5. Use of the following micro-nano bubble-containing water as the water for dilution of the organic acid is preferable, because it leads to increase in amount of the body fluid excreted from the earthworms.

Instead of bringing the earthworms into contact with the organic acid powder or the concentrated aqueous organic acid solution followed by dilution as soon as possible as described above, an aqueous organic acid solution may be prepared beforehand to have a pH adjusted in the range of 2 to 5 and the earthworms may be immersed therein, and the aqueous organic acid solution containing micro-nano bubbles can also be used. The period when the living earthworm exhibits the self-defending function varies to some extent, because about 65% of the living earthworm tissue is moisture, and thus, there is some periodical allowance for the self-protecting function. However, because death of the living earthworms is undesirable, care should be given to the control of the period during which the living earthworms are placed under an unpleasant living environment. The period may vary according to the condition used, but normally in the range of 3 to 180 minutes. Besides the dilution with water, the pH can be adjusted by neutralization with alkali or use of buffer solution. Use of such an organic acid is effective in making the earthworm excrete the digest remaining in the digestive organ as described above and also in sterilizing undesired microbes that cannot be removed by water washing because of the microbicide action of the organic acid.

The living earthworms may be brought into contact with a hydroxycarboxylic acid, as the method of generating an unpleasant living environment. In this case, the contact with hydroxycarboxylic acid may be carried out by any method, but preferably, the living earthworms are added with a crystalline hydroxycarboxylic acid powder by spraying followed by addition of water immediately for dilution of the hydroxycarboxylic acid to adjust the pH of the aqueous acidic solution to a pH in the range of 2 to 5 and the earthworm mixture is stored under the pH condition for 3 to 180 minutes. Prolonged contact between the living earthworms and the hydroxycarboxylic acid powder leads to death of the earthworms with loss of living functions and thus to no excretion of the digest in the digestive tracts, and therefore, the hydroxycarboxylic acid should be diluted with water as soon as possible, normally within 30 seconds or less, preferably 20 seconds or less to adjust the pH of the aqueous acidic solution to a pH in the range of 2 to 5. Besides the dilution with water, the pH can be adjusted by neutralization with alkali or use of buffer solution. Use of the following micro-nano bubble-containing water as the water for dilution of the organic acid is preferable, because it leads to increase in amount of the body fluid excreted from the earthworm. If such a hydroxycarboxylic acid is used, its strong acidity decomposes the skin of the living earthworms and its sterilizing activity causes immediately generation of a living environment unpleasant to the earthworms so that the earthworm tries to improve the living environment by excreting their body fluid under self-protecting function. The contact treatment is also effective in reducing the pathogenic microbes contained in the earthworm body. The hydroxycarboxylic acid, which can form complex compounds with heavy metals, binds to toxic metals such as mercury, cadmium and lead present in the earthworm body, advantageously excreting these metals out of the body. The crystalline hydroxycarboxylic acid used in such a case is not particularly limited in the number of the hydroxyl groups or carboxyl groups contained therein, if the compound is crystalline under the condition used. Thus, it may be a monohydroxy monocarboxylic acid, a monohydroxy polycarboxylic acid, a polyhydroxy monocarboxylic acid or a polyhydroxy polycarboxylic acid. Examples of the hydroxycarboxylic acids include glycolic acid, lactic acid, β-hydroxypropionic acid, α-hydroxy-n-butyric acid, β-hydroxy-n-butyric acid, α-hydroxy-n-valeric acid, β-hydroxy-n-valeric acid, malic acid, α-methylmalic acid, α-hydroxyglutaric acid, β-hydroxyglutaric acid, citric acid and the like, among which lactic acid, malic acid and citric acid are preferable, from the point of availability. These hydroxycarboxylic acids may be used alone or as a mixture of two or more.

Then, the earthworm living bodies after practically complete removal of deposits are washed with purified water and then grounded into liquid or paste-like homogenate. The grinding is carried out, for example, in a homogenizer, a blender, a homomixer, a mashing machine, or a high-pressure cell mill, normally at a temperature of 1 to 25° C., preferably 2 to 15° C. The homogenate is then subjected to freeze-drying. Since the enzymes contained in the earthworm living bodies are inactive when the cells are still alive but react instantaneously with dead cells to generate heat and strong putrefactive odor by putrefaction, for prevention thereof, it is preferable to use freeze-drying under vacuum process in which the homogenate can be cooled rapidly to a temperature of −18° C. to −35° C. to inhibit the enzyme actions and freeze-dried.

For pulverization without deterioration in the pharmacological action inherent to the earthworm, the homogenate should be freeze-dried rapidly, but, on the other hand, extremely rapid freezing is unfavorable, because when the homogenate is frozen in an excessively short period of time, impurities present together with proteins which are the principal component of earthworm paste may not be separated, as they form spotty unfrozen regions. For that reason, the freezing is preferably performed at a low temperature of −18° C. to −35° C. over a period of 20 to 240 hours, more preferably 50 to 170 hours.

During freeze-drying under vacuum, it is important to select a condition allowing favorable removal of water as well as impurities. For that purpose, it is advantageous to perform freeze-drying under vacuum by increasing the temperature stepwise in the range of −60° C. to +90° C. under a pressure of 50 Pa or less taking 10 to 60 hours.

For example, as described above, the homogenate is frozen at a temperature of −18° C. to −35° C. over a period of 20 to 240 hours and freeze-drying under vacuum is performed for 10 to 60 hours by changing a temperature and a pressure stepwise in the range of −60° C. to +90° C. and 40 to 25 Pa, respectively, to obtain a pale yellow dry earthworm powder in the sterile state.

The living earthworms for use in the present invention are preferably washed with water, for example after such a treatment above and before pulverization, but in such a case, micro-nano bubble-containing water can be used favorably as the water used. Use of such water has an advantage that the washing efficiency is improved. The micro-nano bubble means here a bubble having a diameter of 0.01 to 100 μm and the bubble may be air bubble or oxygen bubble. The micro-nano bubble-containing water can be prepared, for example, by a method of producing it by destroying microbubbles under high pressure or by a method of producing bubbles by using a SPG (shirasu porous glass) film. An example of the apparatus producing the microbubble-containing water is a fine bubble-generating/dissolving system having an incorporated slit bubbling device, such as the system manufactured by SPG Technology Co., Ltd.

The method of producing a dry earthworm powder according to the present invention is characterized by heat-treating a dried earthworm product, which is obtained by drying a homogenate of the washed living earthworms, at a temperature of 110° C. or higher but lower than 130° C., preferably at 115 to 125° C. When the heating temperature is lower than 110° C., the dried product may be sterilized insufficiently, while, when it is 130° C. or higher, the enzymes contained in the dried earthworm product may unfavorably be inactivated, leading to decrease in their activities. The heating method is not particularly limited, and examples thereof include methods by blowing hot air, by using heating jacket, by heating by heater on a tray and the like, by using a constant temperature oven and the like.

The heating period is preferably 30 seconds to 130 minutes, more preferably 30 minutes to 90 minutes, and further preferably 60 minutes to 90 minutes. Unfavorably, an excessively short heating period may lead to insufficient sterilization, while an excessively long period to inactivation of the enzymes.

The dry earthworm powder produced by the production method according to the present invention is useful, for example, as a blood pressure-adjusting agent, an anti-hyperlipidemia agent, an anti-diabetes agent and a thrombolytic agent, similarly to the dry earthworm powders prepared by conventional methods. It is also possible to use the powders as an active ingredient in medicines, cosmetics and supplements, by extracting the powder, for example, with purified water or alcohol, centrifuging the solution obtained and fractioning the ingredients by molecular weight.

Hereinafter, the present invention will be described specifically with reference to Examples, but it should be understood that the invention is not limited by these Examples.

Preparation of Dried Earthworm Product

Kilograms of living earthworms of *Lumbricus rubellus* prepared by being kept standing under light for 10 to 50 hours and removed of dirt formed on the skin thereof were placed and spread to a thickness of approximately 5 cm in a flat box and 250 g of citric acid powder was sprayed uniformly thereon, and after 15 seconds, the acid was diluted with 30 liter of purified water. The pH of the aqueous acidic solution immediately after addition of water was 2.25, while the pH at the end of dilution was 2.74.

By the addition of citric acid powder by spraying, the earthworms excreted yellowish body fluid at once and, thus, ammonia, a cause of foul odor, heavy metals such as arsenic hazardous to the body, and hyperfibrinolysis-inhibiting substances were removed.

The living earthworms were then separated from the dirty aqueous citric acid solution, washed with water, and ground into an earthworm paste at 10° C. by using a homogenizer. Then, the earthworm paste was degassed under vacuum, placed in a stainless steel tray, cooled instantaneously to −35° C., and kept at the same temperature, allowing gradual freezing over a period of 50 hours.

The freeze-drying under vacuum was performed in such a manner that the earthworm paste thus frozen was kept standing at a temperature of −35° C. under a pressure of 0 Pa for 2 hours, and the frozen earthworm paste was heated stepwise at a temperature of 25° C. under a pressure of 40 Pa for 10 hours, at a temperature of 40° C. under a pressure of 35 Pa for 14 hours, at a temperature of 65° C. under a pressure of 35 Pa for 12 hours, and finally at a temperature of 80° C. under a pressure of 25 Pa for 6 hours. The processing gave a pale yellow dry earthworm powder having a water content of 8% by mass.

Heat Treatment of Dried Product The dry powder obtained above was heat-treated in RM-50D heater (manufactured by OKAWARA CORPORATION). The heating condition was 110° C., 120° C. or 130° C., as described below, and a part of the dried powder was taken out at an interval of 15 minutes after the power was heated to a specified temperature. With regard to the dried powder taken out, the enzyme activity remaining in the powder was evaluated in a test by the fibrin plate method. First, 20 ml of physiological saline was added to 1 g of the powder; the mixture was shaken at room temperature and 150 rpm for 1 hour and centrifuged at 10000 rpm and 4° C. for 15 minutes; and the supernatant obtained was used as sample. In the fibrin plate method, fibrinogen (manufactured by Sigma Aldrich Corporation) was dissolved in 10 ml of BSB (boron-physiological saline buffer solution, pH 7.8) at a final concentration of 0.6% and thrombin was added to a concentration of 5.0 U/ml, for preparation of a fibrin plate; 30 µl of the sample was placed on the fibrin plate; and the area of the fibrinolysis window generated after incubation at 37° C. for 4 hours was determined. The results obtained are summarized in the following Table 1. The test by the fibrin plate method was repeated for three times, and the mean area was determined. In addition, the graph showing the results obtained is shown in FIG. 1.

Heating Condition

EXAMPLE 1

| Run Number | Temperature | Cumulative Heating Period | Period held at the Temperature |
|---|---|---|---|
| 110-60-0 | 110° C. | 60 minutes | 0 minute |
| 110-75-15 | 110° C. | 75 minutes | 15 minutes |
| 110-90-30 | 110° C. | 90 minutes | 30 minutes |
| 110-105-45 | 110° C. | 105 minutes | 45 minutes |
| 110-120-60 | 110° C. | 120 minutes | 60 minutes |
| 110-135-75 | 110° C. | 135 minutes | 75 minutes |
| 110-150-90 | 110° C. | 150 minutes | 90 minutes |

EXAMPLE 2

| Run Number | Temperature | Cumulative Heating Period | Period held at the Temperature |
|---|---|---|---|
| 120-40-0 | 120° C. | 40 minutes | 0 minute |
| 120-55-15 | 120° C. | 55 minutes | 15 minutes |
| 120-70-30 | 120° C. | 70 minutes | 30 minutes |
| 120-85-45 | 120° C. | 85 minutes | 45 minutes |
| 120-100-60 | 120° C. | 100 minutes | 60 minutes |
| 120-115-75 | 120° C. | 115 minutes | 75 minutes |
| 120-130-90 | 120° C. | 130 minutes | 90 minutes |

COMPARATIVE EXAMPLE 1

| Run Number | Temperature | Cumulative Heating Period | Period held at the Temperature |
|---|---|---|---|
| 130-40-0 | 130° C. | 40 minutes | 0 minute |
| 130-55-15 | 130° C. | 55 minutes | 15 minutes |
| 130-70-30 | 130° C. | 70 minutes | 30 minutes |
| 130-85-45 | 130° C. | 85 minutes | 45 minutes |
| 130-100-60 | 130° C. | 100 minutes | 60 minutes |
| 130-115-75 | 130° C. | 115 minutes | 75 minutes |
| 130-130-90 | 130° C. | 130 minutes | 90 minutes |

TABLE 1

| | | Lysis Area, mm$^2$ | | | |
|---|---|---|---|---|---|
| | | Mean | First time | Second time | Third time |
| | Control* | 495.0 | 508.2 | 488.4 | 488.4 |
| Example 1 | 110-60-0 | 453.7 | 440.9 | 460.1 | 460.1 |
| | 110-75-15 | 442.5 | 424.3 | 443.1 | 460.1 |
| | 110-90-30 | 427.2 | 406.0 | 434.7 | 441.0 |
| | 110-105-45 | 421.5 | 422.1 | 426.2 | 416.1 |
| | 110-120-60 | 408.7 | 408.0 | 422.2 | 396.0 |
| | 110-135-75 | 412.7 | 416.0 | 408.0 | 414.0 |
| | 110-150-90 | 411.4 | 406.0 | 418.2 | 410.0 |
| Example 2 | 120-40-0 | 421.6 | 420.2 | 430.5 | 414.1 |
| | 120-55-15 | 396.7 | 398.0 | 398.0 | 394.0 |
| | 120-70-30 | 368.1 | 370.6 | 355.3 | 378.3 |
| | 120-85-45 | 361.6 | 361.0 | 359.1 | 364.8 |
| | 120-100-60 | 355.3 | 351.5 | 355.3 | 359.1 |
| | 120-115-75 | 330.0 | 336.7 | 325.8 | 327.6 |
| | 120-130-90 | 322.2 | 329.4 | 313.2 | 324.0 |
| Comparative Example 1 | 130-40-0 | 293.0 | 294.1 | 290.7 | 294.1 |
| | 130-55-15 | 196.0 | 191.8 | 198.8 | 197.4 |
| | 130-70-30 | 158.5 | 152.5 | 151.3 | 171.6 |
| | 130-85-45 | 132.6 | 128.8 | 134.5 | 136.8 |
| | 130-100-60 | 122.1 | 124.3 | 121.0 | 121.0 |
| | 130-115-75 | 112.3 | 115.5 | 111.1 | 110.2 |
| | 130-130-90 | 99.0 | 103.0 | 98.0 | 96.0 |

*Control: unheated dry powder

The results in Table 1 and the graph of FIG. 1 clearly show that the activity of the enzymes contained in the dry earthworm powder is preserved sufficiently after the heating at 110° C. (Example 1) or at 120° C. (Example 2), although some of it is lost. In contrast, the activity of the enzymes contained in the dry earthworm powder is lost rapidly by heating at 130° C. (Comparative Example 1) as obvious by comparison of the activities when the heating temperature reached just 130° C. (130-40-0) and those kept at 130° C. (130-55-15 and later).

Determination of Cell Count

As described above, 1 g each of the dry powders each heat-treated at 120° C. (Examples 2-1 to 2-5), at 80° C. for 60 minutes (Comparative Example 2-1), at 90° C. for 60 minutes (Comparative Example 2-2), and at 100° C. for 60 minutes (Comparative Example 2-3) was dissolved in 20 ml of water, to give a test solution; the general viable cell count thereof was determined by the standard agar plate incubation method; the coliform bacterial count was determined by the synthetic enzyme substrate medium method; and the thermophilic bacterial count by the method described in the Standard Methods of Analysis in Food Safety Regulation (heating condition: boiling, 10 minutes). The results obtained are summarized in the following Table 2.

TABLE 2

| | General viable cell count (CFU/g) | Coliform bacterial count (CFU/g) | Thermophilic bacterial count (CFU/g) |
|---|---|---|---|
| Control* | 94,000 | Negative (less than 10) | 3,500 |
| 120-70-30 (Example 2-1) | 440 | Negative (less than 10) | 10 |
| 120-85-45 (Example 2-2) | 400 | Negative (less than 10) | Not detected |
| 120-100-60 (Example 2-3) | 220 | Negative (less than 10) | Not detected |
| 120-115-75 (Example 2-4) | 160 | Negative (less than 10) | Not detected |
| 120-130-90 (Example 2-5) | 50 | Negative (less than 10) | 10 |
| 80° C. (Comparative Example 2-1) | 38,500 | Negative (less than 10) | 1,400 |
| 90° C. (Comparative Example 2-2) | 18,800 | Negative (less than 10) | 1,100 |
| 100° C. (Comparative Example 2-3) | 9,400 | Negative (less than 10) | 620 |

*Control: unheated dry powder

As obvious from the results of Comparative Examples 2-1 to 2-3 in Table 2, the heat treatment at 80° C., 90° C. or 100° C. resulted in survival of many general viable cells and thermophilic bacteria, although *Escherichia coli* was sterilized. In contrast, as obvious from the results in Examples 2-1 to 2-5, heat treatment at 120° C. led to reduction of all of the counts of general viable cells, *Escherichia coli*, and thermophilic bacteria to 1000 CFU/g or less, demonstrating its sufficient effectiveness in sterilization.

The results in the Examples clearly show that the dry earthworm powders produced by the production method according to the present invention retained an enzyme activity similar to those observed in dry earthworm powders prepared by conventional methods and, in addition, were sufficiently sterilized.

What is claimed is:

1. A method of producing a dry earthworm powder which comprises the steps of:
   grinding living earthworms into a homogenate;
   freeze-drying the homogenate; and
   heat-treating the dried product at a temperature in the range of 110° C. or higher but lower than 130° C.

2. The method of producing a dry earthworm powder according to claim 1, wherein the grinding step is preceded by a process for preparation of the living earthworms comprising the steps of:
   standing the living earthworms under light for 10 to 50 hours;
   removing the dirt formed on the skin thereof,
   bringing the earthworms into contact with an organic acid for 30 seconds or less;
   diluting the acid with addition of water to adjust the pH of the aqueous acidic solution to a pH in the range of 2 to 5;
   standing the earthworm mixture under the pH condition for 3 to 180 minutes; and then washing the earthworms with water.

3. The method of producing a dry earthworm powder according to claim 2, wherein the water washing is carried out with water containing micro-nano bubbles.

4. The method of producing a dry earthworm powder according to claim 3, wherein the freeze-drying is carried out under vacuum after the homogenate is frozen at −18° C. to 35° C. for 20 to 240 hours.

5. The method of producing a dry earthworm powder according to claim 2, wherein the freeze-drying is carried out under vacuum after the homogenate is frozen at −18° C. to −35° C. for 20 to 240 hours.

6. The method of producing a dry earthworm powder according to claim 1, wherein the grinding step is preceded by a process for preparation of the living earthworms comprising the steps of:
   standing the living earthworms under light for 10 to 50 hours;
   removing the dirt formed on the skin thereof,
   immersing the earthworms in an aqueous solution of an organic acid having a pH adjusted beforehand in the range of 2 to 5;
   standing the earthworm mixture under the pH condition for 3 to 180 minutes; and then washing the earthworms with water.

7. The method of producing a dry earthworm powder according to claim 6, wherein the water washing is carried out with water containing micro-nano bubbles.

8. The method of producing a dry earthworm powder according to claim 6, wherein the freeze-drying is carried out under vacuum after the homogenate is frozen at −18° C. to −35° C. for 20 to 240 hours.

9. The method of producing a dry earthworm powder according to claim 1, wherein the grinding step is preceded by a process for preparation of the living earthworms comprising the steps of:
   standing the living earthworms under light for 10 to 50 hours;
   removing the dirt formed on the skin thereof,
   bringing the earthworms into contact with a crystalline hydroxycarboxylic acid powder for 30 seconds or less;
   diluting the acid with addition of water to adjust the pH of the aqueous acidic solution to a pH in the range of 2 to 5;
   standing the earthworm mixture under the pH condition for 3 to 180 minutes; and then washing the earthworms with water.

10. The method of producing a dry earthworm powder according to claim 9, wherein the water washing is carried out with water containing micro-nano bubbles.

11. The method of producing a dry earthworm powder according to claim 9, wherein the freeze-drying is carried out under vacuum after the homogenate is frozen at −18° C. to −35° C. for 20 to 240 hours.

12. The method of producing a dry earthworm powder according to claim 1, wherein the freeze-drying is carried out under vacuum after the homogenate is frozen at −18° C. to −35° C. for 20 to 240 hours.

* * * * *